US012566153B2

(12) United States Patent
Maney, Jr. et al.

(10) Patent No.: US 12,566,153 B2
(45) Date of Patent: Mar. 3, 2026

(54) PRINTED ELECTRODE

(71) Applicant: Roche Sequencing Solutions, Inc., Pleasanton, CA (US)

(72) Inventors: J. William Maney, Jr., Emerald Hills, CA (US); David Bruce Robinson, Hayward, CA (US); Markus Wallgren, Los Altos Hills, CA (US); Robert A. Yuan, San Jose, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 587 days.

(21) Appl. No.: 17/805,196

(22) Filed: Jun. 2, 2022

(65) Prior Publication Data

US 2022/0299472 A1    Sep. 22, 2022

Related U.S. Application Data

(63) Continuation of application No. 15/487,825, filed on Apr. 14, 2017, now abandoned, which is a continuation of application No. 14/575,938, filed on Dec. 18, 2014, now Pat. No. 9,658,190.

(51) Int. Cl.
| | |
|---|---|
| *G01N 27/447* | (2006.01) |
| *C12Q 1/6869* | (2018.01) |
| *G01N 27/403* | (2006.01) |
| *G01N 33/487* | (2006.01) |

(52) U.S. Cl.
CPC ..... *G01N 27/44791* (2013.01); *C12Q 1/6869* (2013.01); *G01N 27/403* (2013.01); *G01N 33/48721* (2013.01)

(58) Field of Classification Search
CPC ....... G01N 27/44791; G01N 33/48721; G01N 27/403; C12Q 1/6869
See application file for complete search history.

(56) References Cited

U.S. PATENT DOCUMENTS

| | | | |
|---|---|---|---|
| 2011/0050200 A1* | 3/2011 | Tartagni ................. | G01N 15/12 324/71.4 |
| 2012/0190126 A1* | 7/2012 | Eshoo .................. | C12Q 1/6806 422/547 |
| 2015/0153302 A1* | 6/2015 | Davis ................. | G01N 27/3278 204/403.08 |

(Continued)

OTHER PUBLICATIONS

Ramachandraiah et al., "Dean flow-coupled inertial focusing in curved channels," 2014, Biomicrofluidics, 8(3), 034117 (Year: 2014).*

(Continued)

*Primary Examiner* — Luan V Van
*Assistant Examiner* — Kaylee Tseng
(74) *Attorney, Agent, or Firm* — Winston Chu

(57) ABSTRACT

A nanopore based sequencing chip package is disclosed. The nanopore based sequencing chip package includes a reservoir defined by a plurality of surfaces. The chip package includes a nanopore cell array comprising a plurality of nanopore sensor cells enclosed by the reservoir. Each nanopore sensor cell has a working electrode. At least one surface of the reservoir is configured to be in contact with a conducting fluid when the conducting fluid is flowing through the reservoir. The chip package further includes a counter electrode disposed on the at least one surface of the reservoir.

6 Claims, 10 Drawing Sheets

(56) References Cited

U.S. PATENT DOCUMENTS

2016/0138908 A1* 5/2016 Khan ................... B01L 3/5027
73/800

OTHER PUBLICATIONS

Lee et al., "3D printed modules for integrated microfluidic devices,"
2014, RSC Advances, vol. 4, pp. 32876-32880 (Year: 2014).*

* cited by examiner

100

Bulk Electrolyte ⟋114

PRINTED ELECTRODE

CROSS REFERENCE TO OTHER APPLICATIONS

This application is a continuation of co-pending U.S. patent application Ser. No. 15/487,825, filed Apr. 14, 2017, which is a continuation of U.S. patent application Ser. No. 14/575,938 entitled PRINTED ELECTRODE filed Dec. 18, 2014, each of which is incorporated herein by reference for all purposes.

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore based sequencing chip may be used for DNA sequencing. A nanopore based sequencing chip incorporates a large number of sensor cells configured as an array. For example, an array of one million cells may include 1000 rows by 1000 columns of cells.

Figure 1:
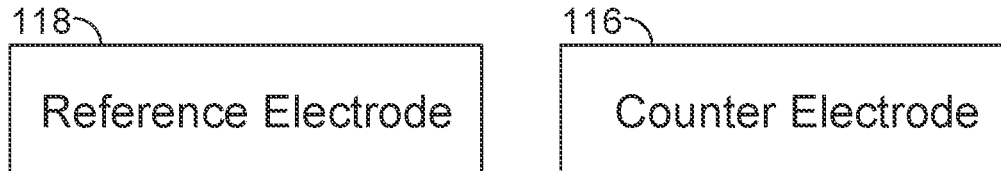
FIG. 1 illustrates an embodiment of a cell 100 in a nanopore based sequencing chip.
Figure 1:
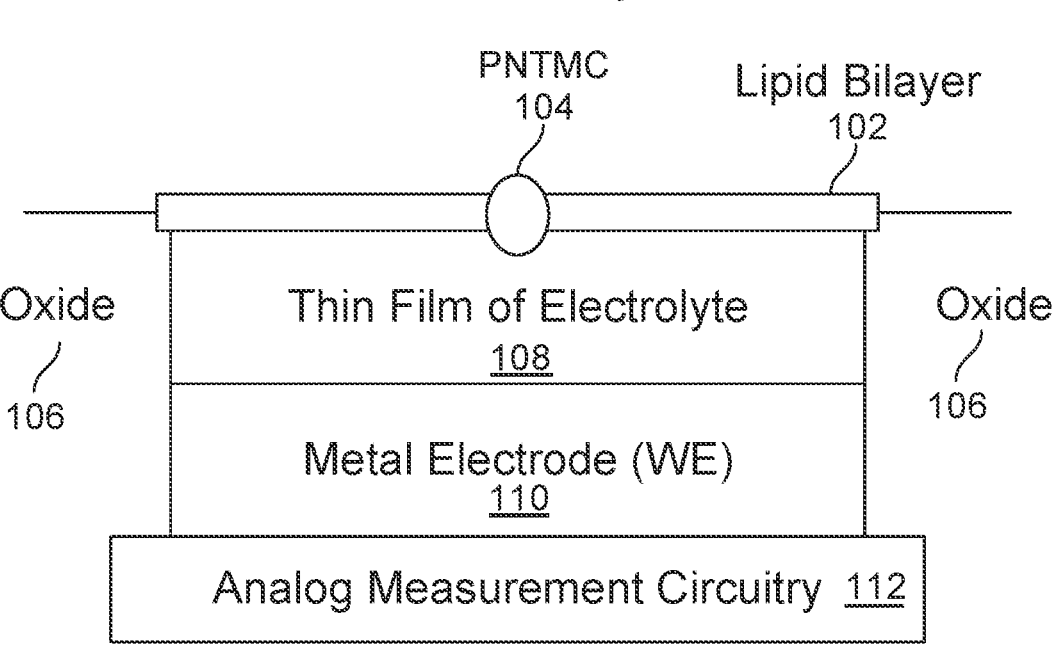

FIG. 1 illustrates an embodiment of a cell 100 in a nanopore based sequencing chip. A lipid bilayer 102 is formed over the surface of the cell. The bulk electrolyte 114 containing soluble protein nanopore transmembrane molecular complexes (PNTMC) and the analyte of interest is placed directly onto the surface of the cell. A single PNTMC 104 is inserted into lipid bilayer 102 by electroporation. The individual lipid bilayers in the array are not connected to each other either chemically or electrically. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a thin film of electrolyte 108. Metal electrode 110 is also referred to as a working electrode (WE). The thin film of electrolyte 108 is isolated from the bulk electrolyte 114 by the ion-impermeable lipid bilayer 102. PNTMC 104 crosses lipid bilayer 102 and provides the only path for ionic current to flow in the bulk liquid between metal electrode 110 and a counter electrode 116 positioned on the other side of PNTMC 104 when a voltage is applied across the electrodes. Counter electrode 116 is a common electrode that is shared by the cells in the nanopore array. Because the signal levels are very small, extraneous noise from the fluid and other components in the system may have an effect on the measurements. These extraneous signals may be reduced by including a third reference electrode 118. The reference electrode is a common electrode that is shared by the cells of the nanopore array.

Figure 2:
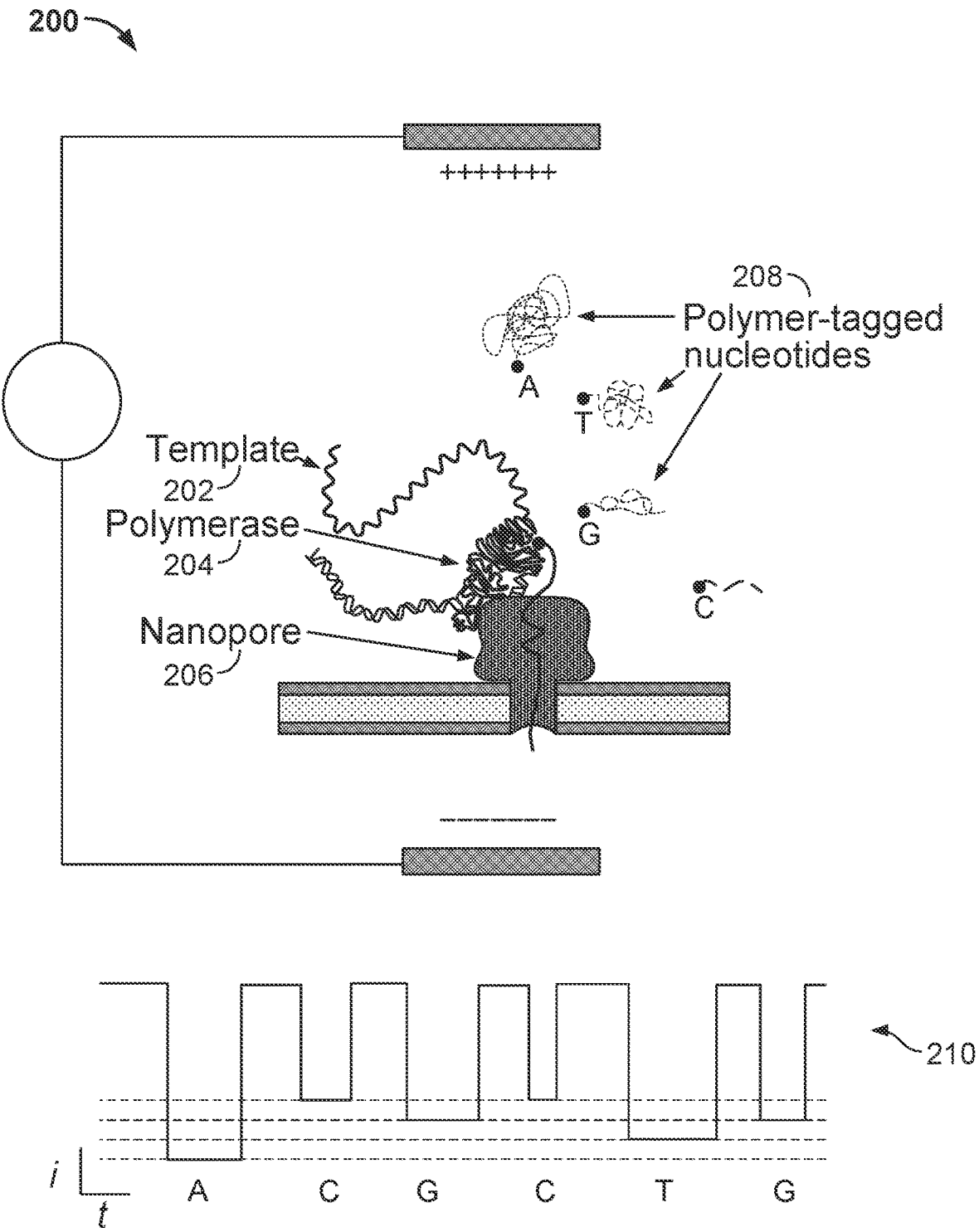
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. After polymerase catalyzed incorporation of the correct nucleotide, the tag-attached polyphosphate held in the barrel of nanopore 206 generates a unique ionic current blockade signal 210, thereby identifying the added base (A, G, C, or T) electronically due to the tags' distinct chemical structures.

Figure 3:
FIG. 3 illustrates an embodiment of a cell about to perform nucleotide sequencing with pre-loaded tags.
Figure 3:
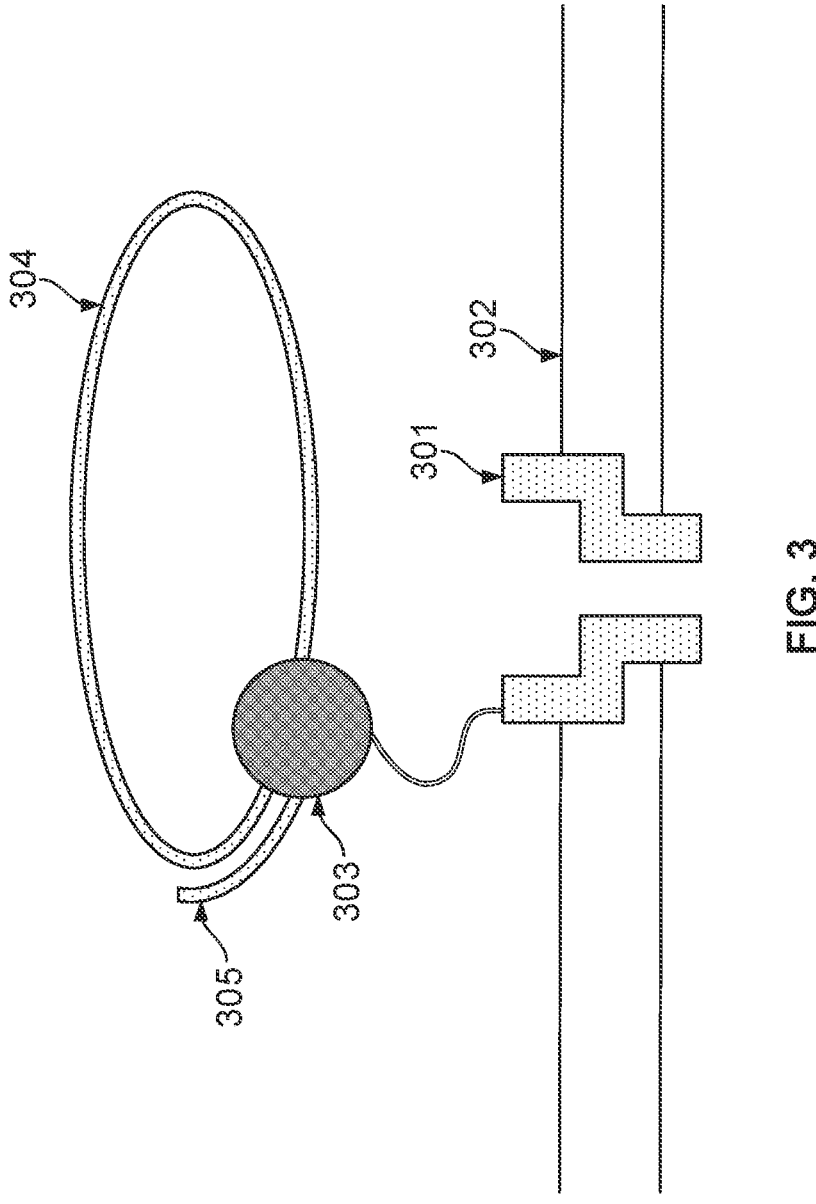

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a single stranded nucleic acid molecule 304 to be sequenced. In some embodiments, single or double stranded nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
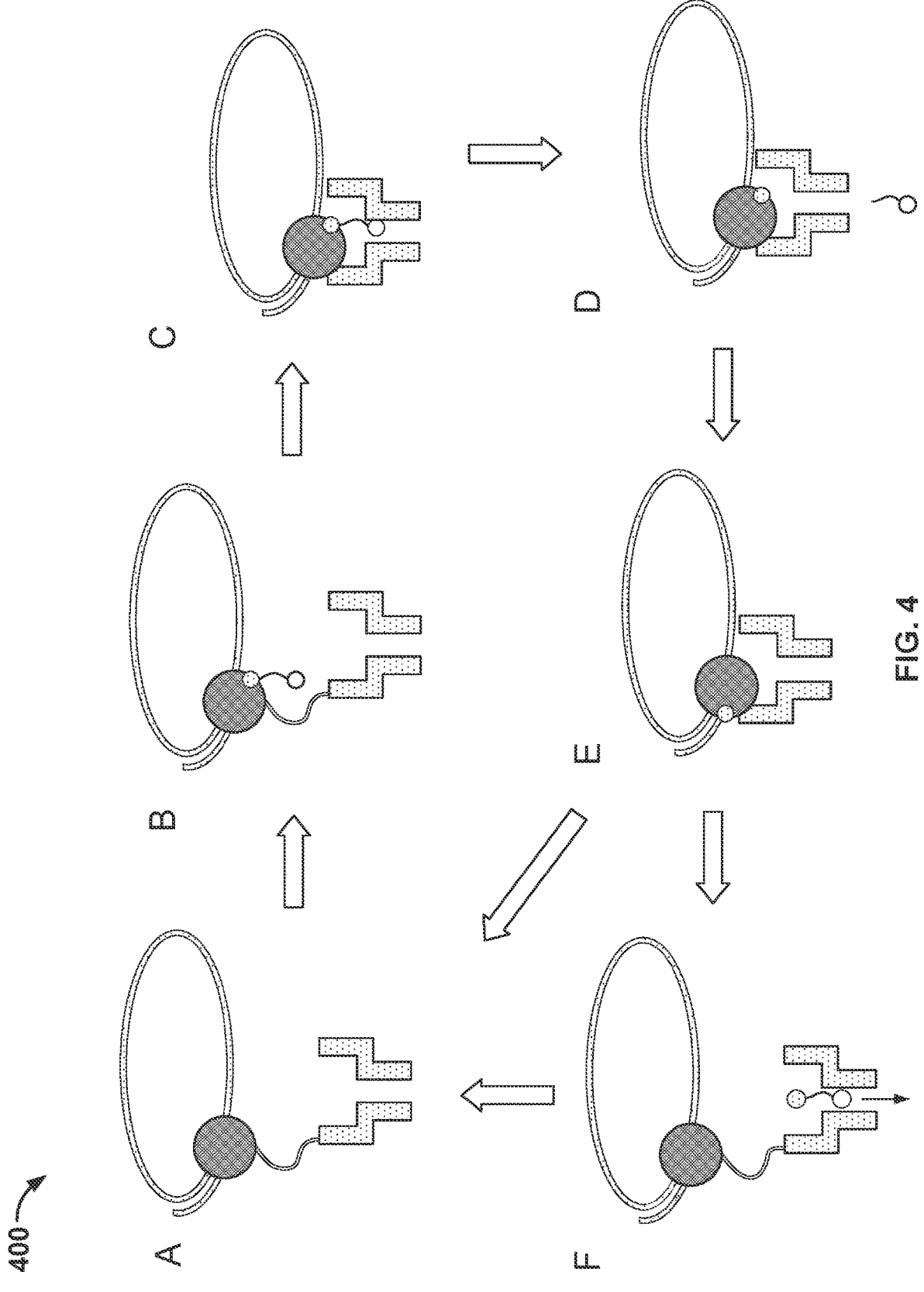
FIG. 4 illustrates an embodiment of a process 400 for nucleic acid sequencing with pre-loaded tags.

FIG. 4 illustrates an embodiment of a process 400 for nucleic acid sequencing with pre-loaded tags. Stage A illustrates the components as described in FIG. 3. Stage C shows the tag loaded into the nanopore. A "loaded" tag may be one that is positioned in and/or remains in or near the nanopore for an appreciable amount of time, e.g., 0.1 millisecond (ms) to 1000 ms. In some cases, a tag that is pre-loaded is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are base paired with the single stranded nucleic acid molecule (e.g., A with T and G with C). However, some of the associated tagged nucleotides are not base paired with the single stranded nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage D. For example, a non-paired nucleotide is rejected by the polymerase at stage B or shortly after the process enters stage C.

Before the polymerase is docked to the nanopore, the current passing through the nanopore is ~30 picoamps (pA).

At stage C, the current flowing through the nanopore is about 6 pA, 8 pA, 10 pA, or 12 pA, each amperage corresponding to one of the four types of tagged nucleotides. The polymerase undergoes an isomerization and a transphosphorylation reaction to incorporate the nucleotide into the growing nucleic acid molecule and release the tag molecule. At stage D, the released tag passes through the nanopore. The tag is detected by the nanopore. In particular, as the tag is held in the nanopore, a unique ionic current blockade signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
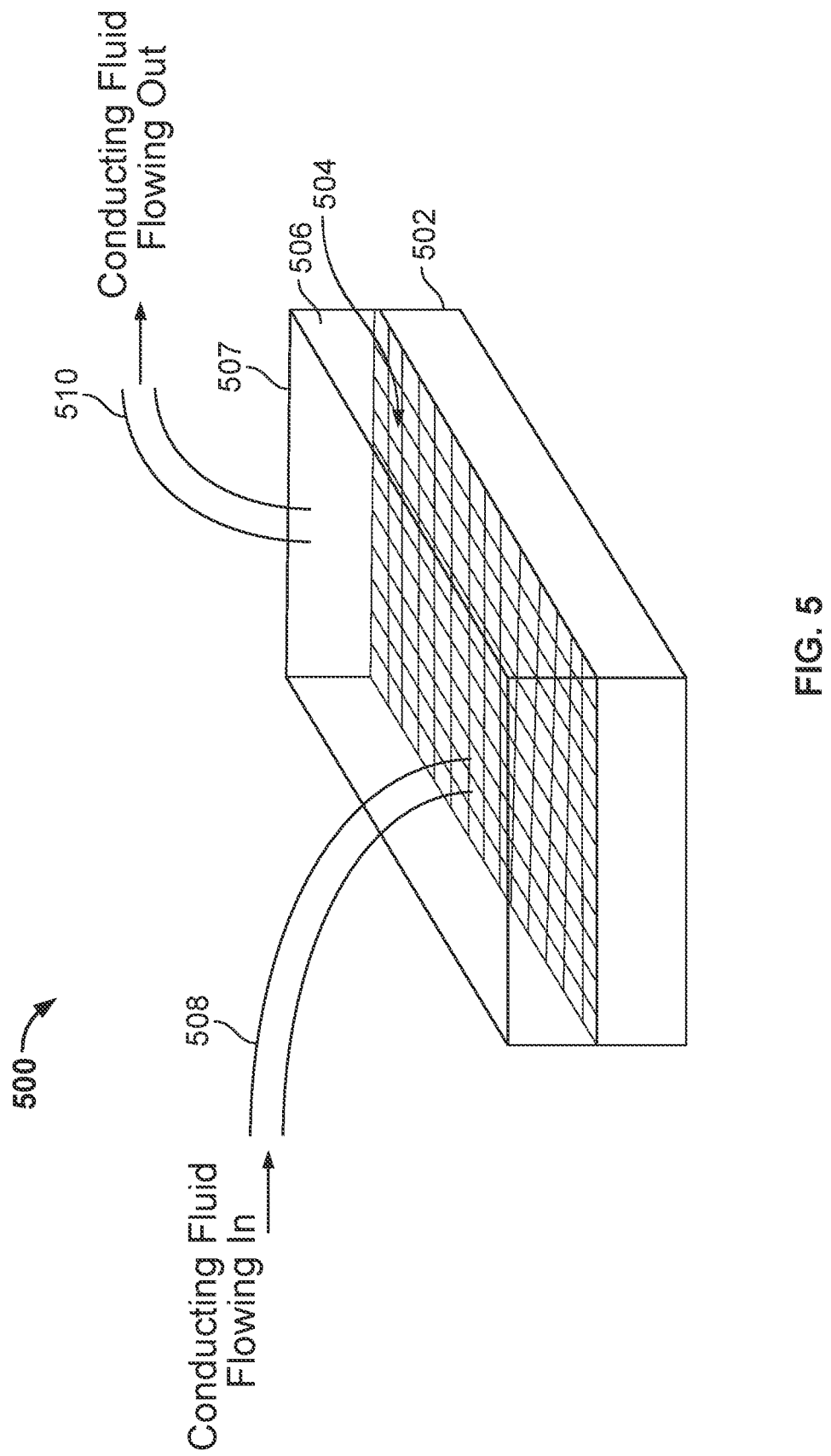
FIG. 5 illustrates an embodiment of a nanopore based sequencing chip package 500.

FIG. 5 illustrates an embodiment of a nanopore based sequencing chip package 500. Nanopore based sequencing chip package 500 includes a nanopore based sequencing chip 502. Nanopore based sequencing chip 502 incorporates a large number of nanopore sensor cells configured as a nanopore array 504. For example, an array of one million cells may include 1000 rows by 1000 columns of cells. Nanopore based sequencing chip package 500 further includes a reservoir 506 that is mounted on top of nanopore based sequencing chip 502 and encloses the nanopore cells. An ingress tube 508 directs conducting fluid into reservoir 506, and an egress tube 510 directs the conducting fluid out of reservoir 506. In some embodiments, the counter electrode and the reference electrode are sintered silver/silver-chloride (Ag—AgCl) pellets or wires. These electrodes may be inserted into the tubes (egress tube 510 or ingress tube 508).

Figure 6:
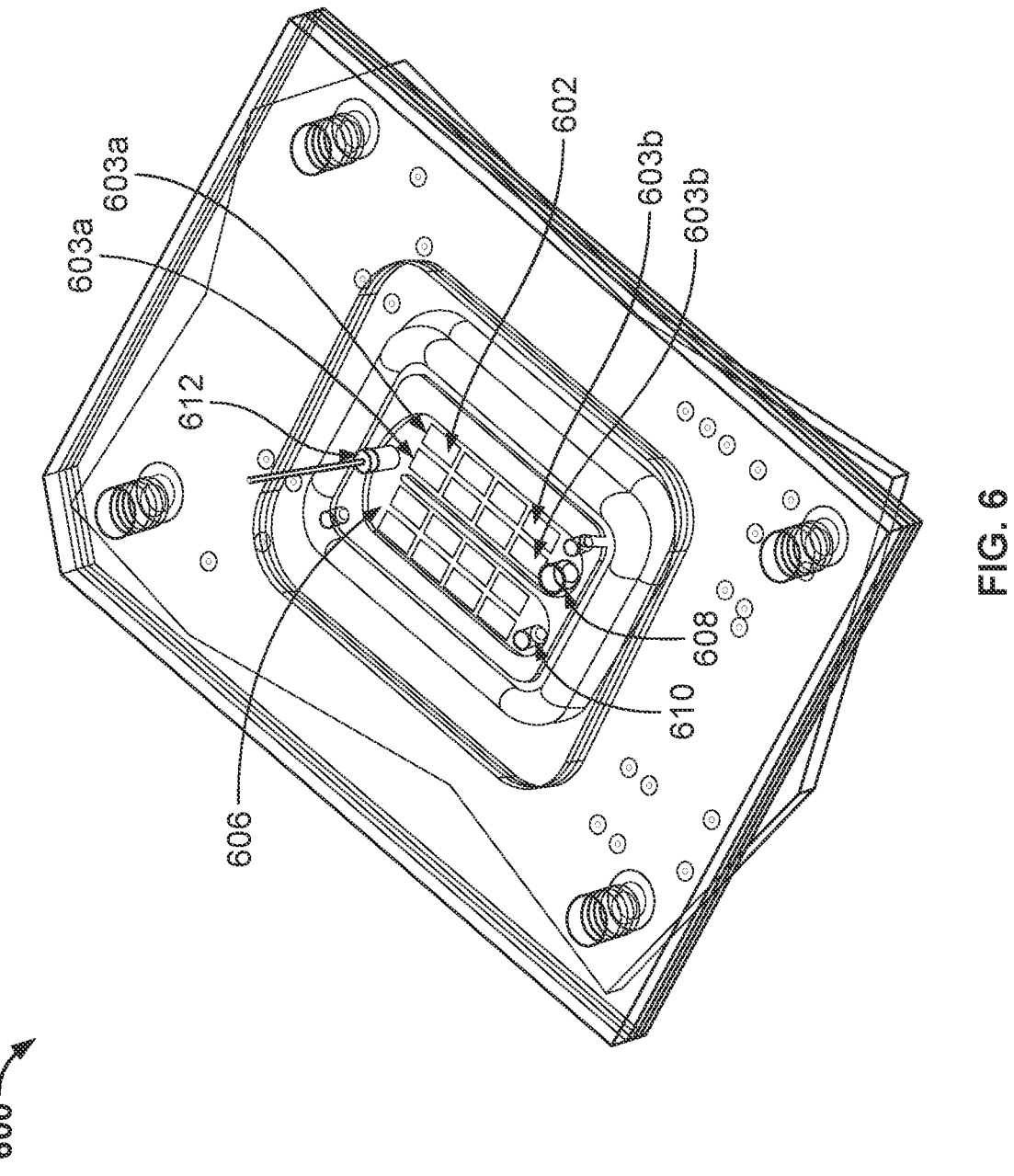
FIG. 6 illustrates another embodiment of a nanopore based sequencing chip package 600.

FIG. 6 illustrates another embodiment of a nanopore based sequencing chip package 600. Nanopore based sequencing chip package 600 includes a nanopore based sequencing chip 602. Nanopore based sequencing chip 602 incorporates a large number of nanopore sensor cells configured as a plurality of nanopore banks 603 (a and b). For example, sixteens banks of 8K cells form a nanopore array that includes a total of 128K cells. Nanopore based sequencing chip package 600 further includes a reservoir 606 that is mounted on top of nanopore based sequencing chip 602 and encloses the nanopore cells. An ingress tube 608 directs conducting fluid into reservoir 606 and an egress tube 610 directs the conducting fluid out of reservoir 606. In some embodiments, the counter electrode and the reference electrode are sintered silver/silver-chloride (Ag—AgCl) pellets or wires. A counter electrode 612 may be immersed in the conducting fluid within reservoir 606.

However, the embodiments shown in FIG. 5 and FIG. 6 have a number of drawbacks. The sintered electrodes that are commerically available off-the-shelf are relatively expensive. In addition, installation of the electrodes into the reservoir requires proper alignment and sealing steps that can be labor intensive and complex.

More importantly, since the size of the sintered counter electrode is small compared to the nanopore array, the sintered counter electrode is closer to some cells (and thus their corresponding working electrodes) but further away from others. For example, as shown in FIG. 6, nanopore banks 603a are closer to sinter counter electrode 612 than nanopore banks 603b. As the nanopore based sequencing chip is scaled to include more and more cells, the current flowing in the conducting fluid increases. As the current increases, the voltage drop due to the conducting fluid resistance becomes larger as well. As a result, the voltage seen by a working electrode that is closer to the counter electrode is greater than that seen by a working electrode that is further away from the counter electrode. The variations in voltage among different cells impact the biological mechanisms.

Figure 7:
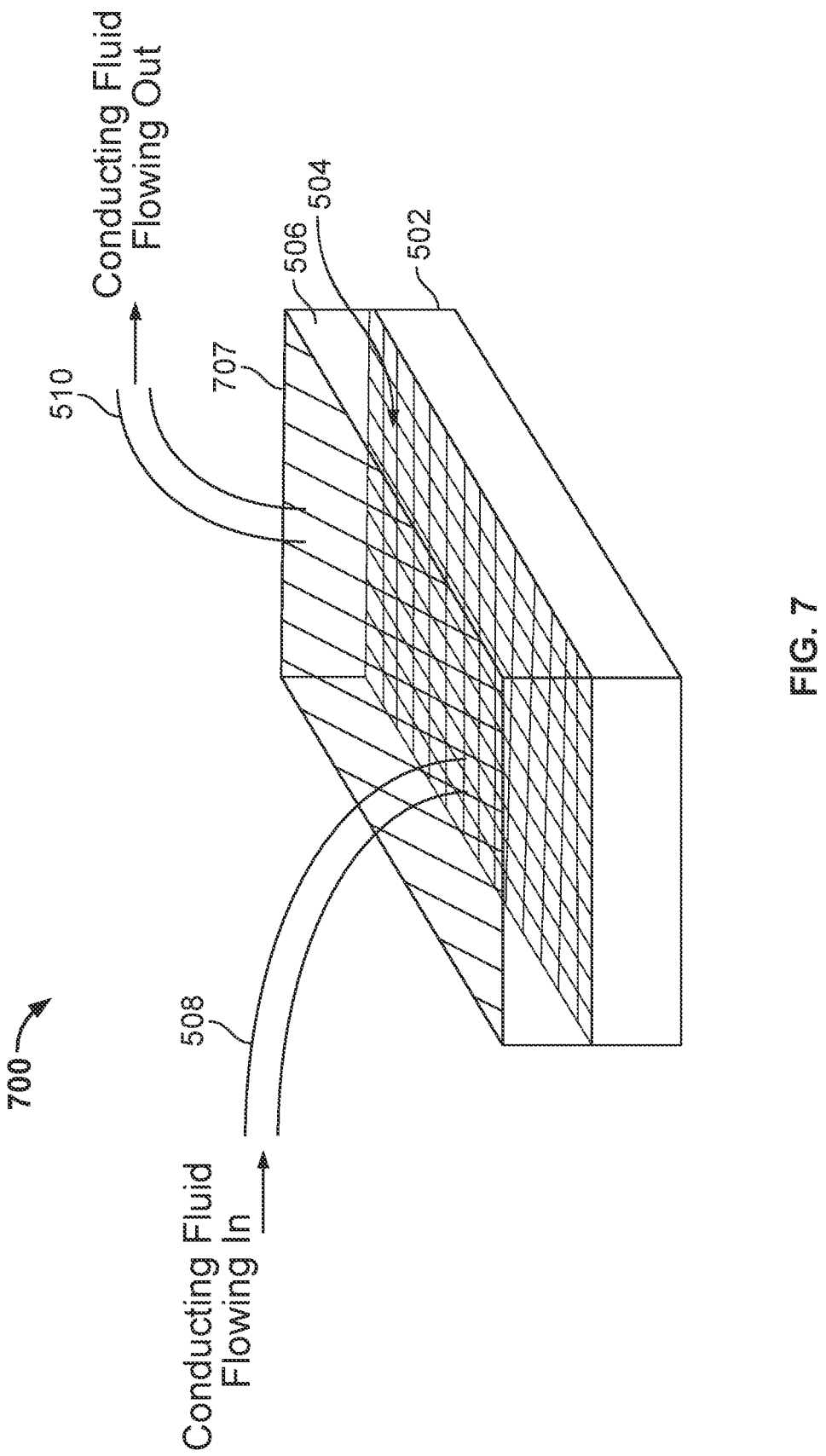
FIG. 7 illustrates an embodiment of a nanopore based sequencing chip package 700 in which the counter electrode is positioned substantially equidistant from each of the nanopore cells and their corresponding working electrodes.

FIG. 7 illustrates an embodiment of a nanopore based sequencing chip package 700 in which the counter electrode is positioned substantially equidistant from each of the nanopore cells and their corresponding working electrodes. With the counter electrode positioned substantially equidistant from each of the nanopore cells, the voltage drop due to the conducting fluid resistance becomes substantially identical for all cells and the variation in voltage among different cells is therefore significantly reduced.

As shown in FIG. 7, the nanopore based sequencing chip package 700 includes a counter electrode 707 that is directly above the nanopore cells and their corresponding working electrodes. For example, counter electrode 707 has a surface area and shape that match the surface area and shape of nanopore array 504 below. In this particular example, since nanopore array 504 has a rectangular shape, counter electrode 707 has a rectangular shape that matches nanopore array 504. However, it is anticipated that the counter electrode may have a shape other than a rectangular shape (e.g., a square or other irregular shapes) to match with a nanopore array in a different shape as well.

In some embodiments, counter electrode 707 is a metal plate that is positioned directly above the nanopore cell array. For example, the metal plate may be disposed on the bottom surface of a roof of reservoir 506 such that the metal plate is in contact with the conducting fluid when the fluid is flowing through the reservoir. In some embodiments, the solid metal plate may be formed using silver-silver chloride (Ag—AgCl). However, other types of metal plates may be used as well.

In some embodiments, counter electrode 707 is formed using a plating process. For example, counter electrode 707 may be formed using an electroplating or ion deposition process in which the material forming the counter electrode is plated onto a flat substrate.

In some embodiments, counter electrode 707 is screen printed on a surface that is positioned directly above the nanopore cell array. For example, Ag—AgCl ink may be screen printed on a flexible printed circuit (FPC) to form a counter electrode and a reference electrode. Each of the two electrodes may be electrically coupled to a voltage source or other control units via the FPC. The FPC may be disposed on the bottom surface of the roof of reservoir 506. The FPC may also be disposed directly below a plastic backing plate, with the plastic backing plate forming the roof of reservoir 506. One of the advantages of screen printing the counter electrode is low cost.

In some embodiments, counter electrode 707 is printed on a surface that is positioned directly above the nanopore cell array. For example, using ink jet printing, counter electrode 707 may be printed directly onto an injection molded flow cell that mounts atop the chip.

Figure 8A:
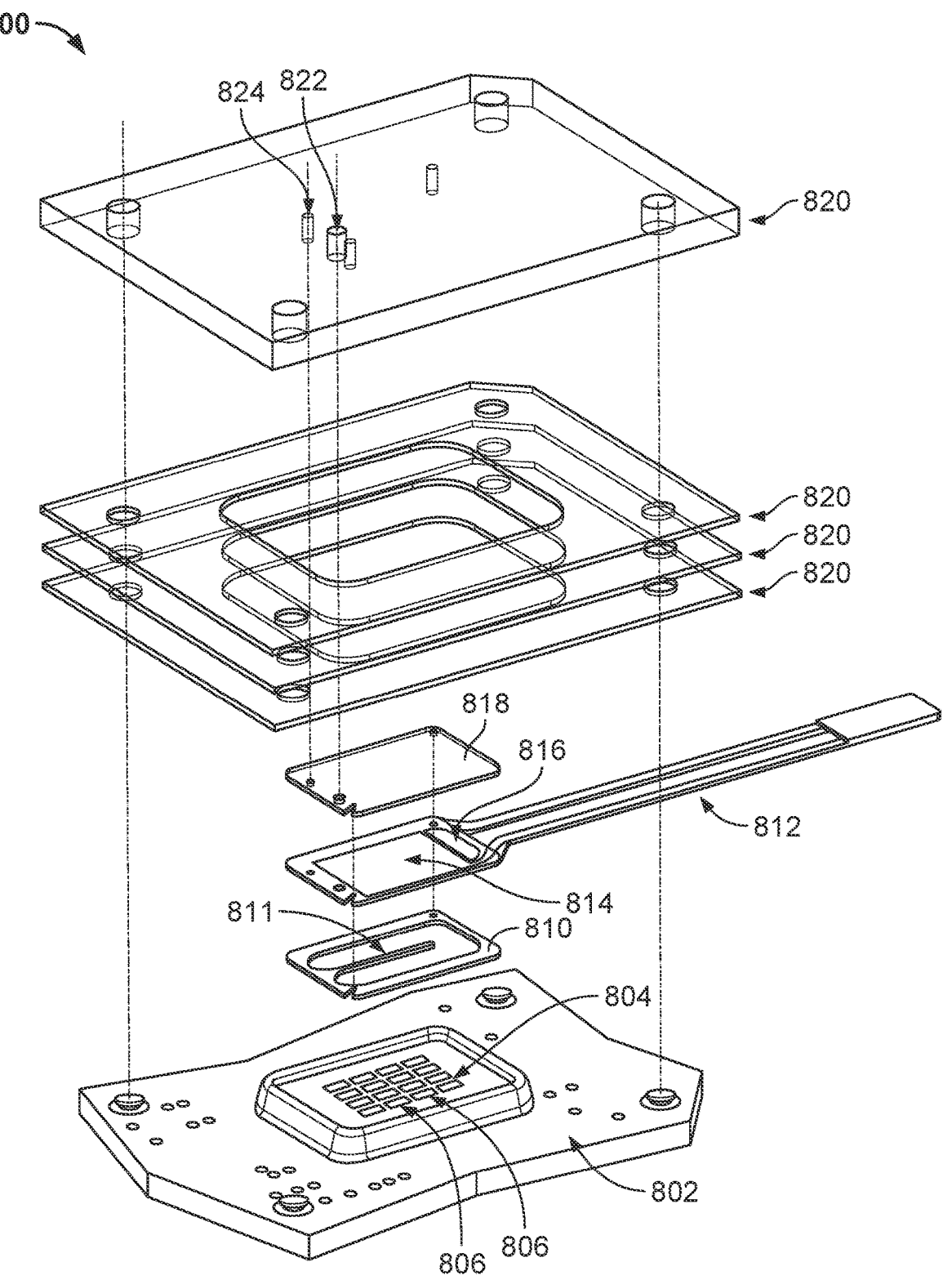
FIG. 8A illustrates the various components and layers of nanopore based sequencing chip package 800.
Figure 8B:
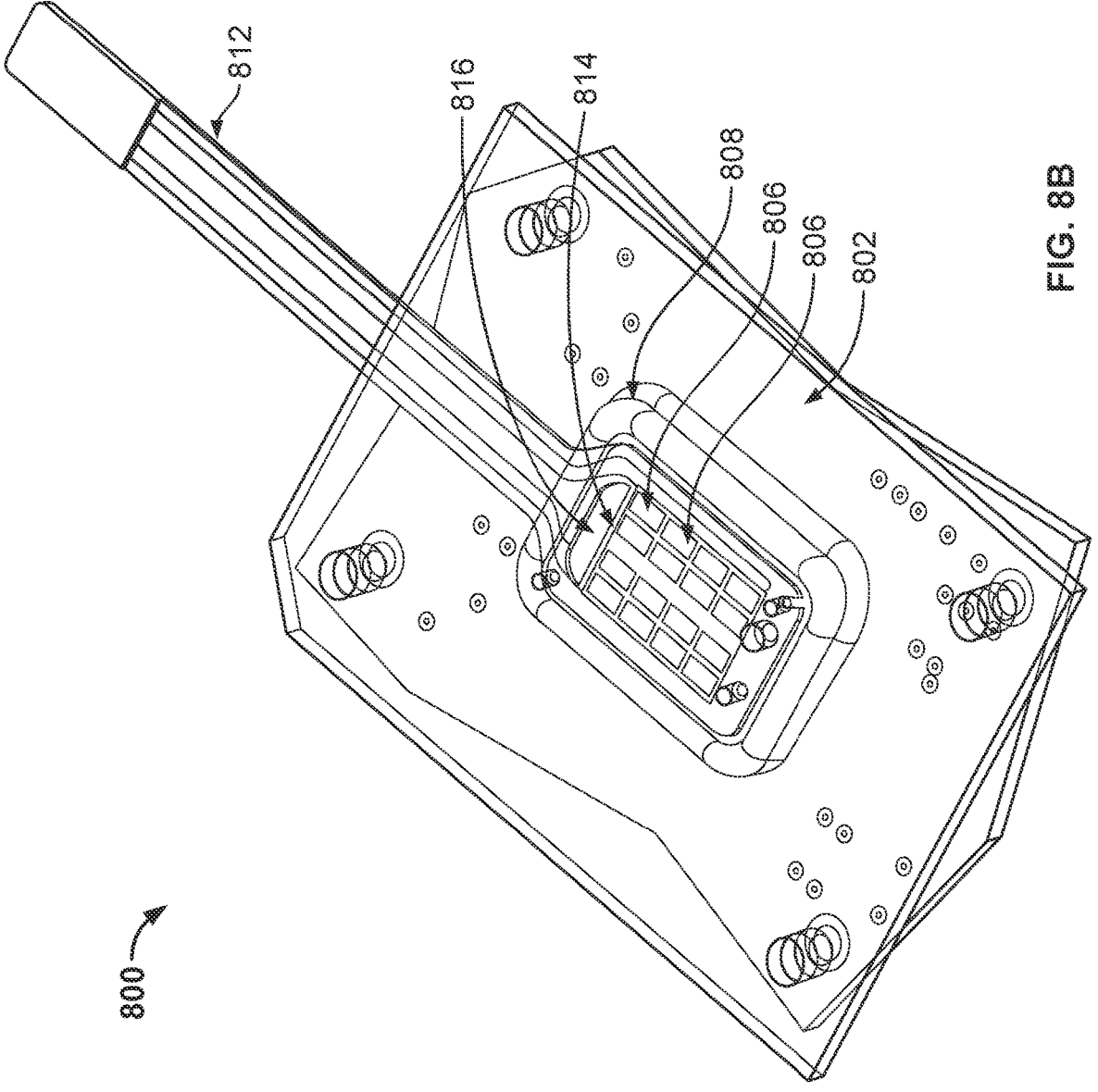
FIG. 8B illustrates nanopore based sequencing chip package 800 when its components and layers are integrated and laminated together.

FIGS. 8A and 8B illustrate an embodiment of nanopore based sequencing chip package 800. FIG. 8A illustrates the various components and layers of nanopore based sequencing chip package 800. FIG. 8B illustrates nanopore based sequencing chip package 800 when its components and layers are integrated and laminated together.

Referring to FIG. 8A and FIG. 8B, nanopore based sequencing chip package 800 includes a nanopore based sequencing chip 804 mounted on a printed circuit board 802. Nanopore based sequencing chip 804 incorporates a large number of nanopore sensor cells configured as a plurality of nanopore banks 806. As shown in FIG. 8A, sixteen nanopore banks of 8K cells form a nanopore array that includes a total of 128K cells. However, it is anticipated that nanopore based sequencing chip 804 may include a nanopore array that has millions of cells arranged in a greater number of nanopore banks or arranged in larger nanopore banks.

Nanopore based sequencing chip package 800 further includes a reservoir that encloses the nanopore cells and the conducting fluid that flows through the reservoir. The reservoir further includes a roof or a top cover. In this example, the roof of the reservoir is a plastic backing plate 818. After plastic backing plate 818 is laminated with a plurality of top cover layers 820 that are attached to printed circuit board 802, the plastic backing plate 818 and the gasket 810 form a sealed reservoir that encloses the nanopore cells and the conducting fluid that flows through the reservoir. The topmost top cover layer 820 includes an ingress 824 and an egress 822. Ingress 824 directs conducting fluid into the reservoir, and egress 822 directs the conducting fluid out of the reservoir.

Nanopore based sequencing chip package 800 further includes a fluid channel gasket 810. Fluid channel gasket 810 allows an even flow of the conducting fluid through the reservoir. Fluid channel gasket 810 includes dividing walls 811 that divide the space within the reservoir into serpentine channels. The serpentine channels may be U-shaped channels, S-shaped channels, and the like. By reducing the width of the channels, more even flow of the conducting fluid through the reservoir can be achieved.

Figure 9:
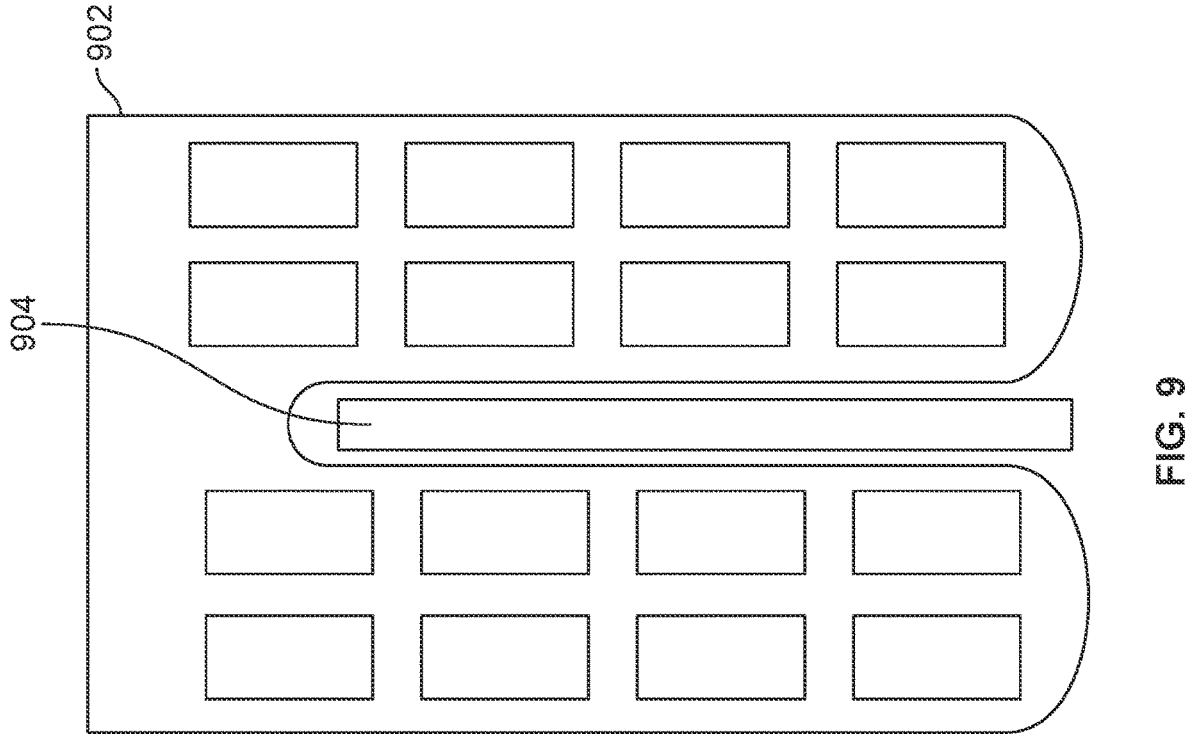
FIG. 9 illustrates that a counter electrode 902 may have a surface area and shape that match the U-shaped channel formed by the fluid channel gasket such that counter electrode 902 is substantially equidistant from each of the nanopore cells and their corresponding working electrodes.

Nanopore based sequencing chip package 800 further includes a counter electrode 814 and a reference electrode 816 that are screen printed on a surface that is positioned directly above the nanopore cell array. In this example, Ag—AgCl ink is screen printed on a flexible printed circuit (FPC) 812 to form counter electrode 814 and reference electrode 816. Each of the two electrodes is electrically coupled to a voltage source or other control units via FPC 812. The portion of FPC 812 that includes counter electrode 814 is disposed on the bottom side of plastic backing plate 818, which forms the roof of the reservoir. As shown in FIGS. 8A and 8B, counter electrode 814 is positioned substantially equidistant from each of the nanopore cells and their corresponding working electrodes. Counter electrode 814 has a surface area and shape that match the nanopore array below. For example, for any particular nanopore cell and its corresponding working electrode, there is a portion of counter electrode 814 that is disposed on a plane that is substantially parallel to the top surface of the nanopore cell and substantially directly above the nanopore cell and its corresponding working electrode such that the portions of the counter electrode are substantially equidistant from their corresponding nanopore sensor cell. In this particular example, since the nanopore array has a rectangular shape, counter electrode 814 has a rectangular shape that matches the nanopore array As shown in FIGS. 8A and 8B, reference electrode 816 is positioned adjacent to counter electrode 814. However, reference electrode 816 may be positioned in other locations. For example, reference electrode 816 may be inserted into the ingress/egress tubes. Reference electrode 816 may also be disposed longitudinally on the bottom side of the roof of the reservoir. For example, FIG. 9 illustrates that a counter electrode 902 may have a surface area and shape that match the U-shaped channel formed by the fluid channel gasket such that counter electrode 902 is substantially equidistant from each of the nanopore cells and their corresponding working electrodes. A reference electrode 904 is disposed longitudinally in the gap between the U-shape.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A sequencing chip package, comprising:
a sequencing chip mounted on a printed circuit board, the sequencing chip comprising an array of sensor cells, wherein each sensor cell comprises a working electrode;

a backing plate configured to be disposed over the printed circuit board to form a fluid tight seal and to enclose an open reservoir over the sequencing chip, wherein the backing plate comprises at least one inlet and at least one outlet that are configured to provide fluid communication with the open reservoir; and
a fluid channel gasket disposed between the backing plate and the sequencing chip, wherein the fluid channel gasket comprises at least one dividing wall that is configured to divide the open reservoir into a U-shaped fluid channel with a U-shaped fluid path over the sequencing chip.

2. The sequencing chip package of claim 1, further comprising a counter electrode disposed on an interior surface of the backing plate, wherein the counter electrode is configured to be positioned over the array of sensor cells.

3. The sequencing chip package of claim 1, wherein the at least one inlet and the at least one outlet are positioned on a first end portion of the backing plate.

4. The sequencing chip package of claim 1, wherein each sensor cell is configured to support a membrane with a nanopore.

5. The sequencing chip package of claim 1, further comprising a counter electrode that is positioned substantially equidistant from each of the sensor cells.

6. The sequencing chip package of claim 5, wherein a voltage drop due to a fluid resistance is substantially identical between each sensor cell and the counter electrode.

\* \* \* \* \*